US012605512B2

(12) United States Patent
Nekouzadeh et al.

(10) Patent No.: US 12,605,512 B2
(45) Date of Patent: Apr. 21, 2026

(54) DRUG DELIVERY DEVICE

(71) Applicant: AMGEN INC., Thousand Oaks, CA (US)

(72) Inventors: Ali Nekouzadeh, Thousand Oaks, CA (US); Carl Conrath, Thousand Oaks, CA (US); Kimberly Sepulveda, Thousand Oaks, CA (US); Jimmie L. Ward, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 655 days.

(21) Appl. No.: 17/767,463

(22) PCT Filed: Oct. 7, 2020

(86) PCT No.: PCT/US2020/054496
§ 371 (c)(1),
(2) Date: Apr. 8, 2022

(87) PCT Pub. No.: WO2021/071886
PCT Pub. Date: Apr. 15, 2021

(65) Prior Publication Data
US 2024/0082502 A1 Mar. 14, 2024

Related U.S. Application Data

(60) Provisional application No. 62/912,316, filed on Oct. 8, 2019.

(51) Int. Cl.
*A61M 5/31* (2006.01)
*A61M 5/20* (2006.01)
*A61M 5/315* (2006.01)

(52) U.S. Cl.
CPC ...... *A61M 5/31578* (2013.01); *A61M 5/2033* (2013.01)

(58) Field of Classification Search
CPC ............ A61M 5/31578; A61M 5/2033; A61M 2005/3238; A61M 5/31511;
(Continued)

(56) References Cited

U.S. PATENT DOCUMENTS

| | | | | |
|---|---|---|---|---|
| 2007/0265568 A1* | 11/2007 | Tsals | ................... | A61M 5/2033 604/890.1 |
| 2017/0232201 A1* | 8/2017 | Holland | .............. | A61M 5/3129 604/218 |
| 2019/0134314 A1* | 5/2019 | Dasbach | ........... | A61M 5/31513 |

OTHER PUBLICATIONS

Written Opinion of the International Searching Authority issued to International application No. PCT/US2020/054496, dated Feb. 4, 2021.
(Continued)

*Primary Examiner* — Tasnim Mehjabin Ahmed
*Assistant Examiner* — Haden Matthew Ritchie
(74) *Attorney, Agent, or Firm* — MARSHALL, GERSTEIN & BORUN LLP

(57) ABSTRACT

A drug delivery device may include a housing having an opening, a drug storage container, a plunger rod, and a drive mechanism. The drug storage container may have an inner surface at least partially defining a drug storage chamber and an outer surface defining an outer diameter. The drug storage container may further include a plunger stopper and a delivery member having an insertion end configured to extend at least partially through the opening during a delivery state. The drive mechanism may be activatable to drive the plunger stopper in a distal direction to expel a drug from the drug storage container through the delivery member. The drive mechanism may have an inner surface with an inner diameter greater than the outer diameter of the outer surface of the drug storage container.

15 Claims, 9 Drawing Sheets

(58) Field of Classification Search
      CPC ............ A61M 5/3158; A61M 5/31591; A61M
                               2005/206; A61M 2005/31518
      See application file for complete search history.

(56)                    References Cited

OTHER PUBLICATIONS

International Search Report issued to International application No.
PCT/US2020/054496, dated Feb. 4, 2021.

* cited by examiner

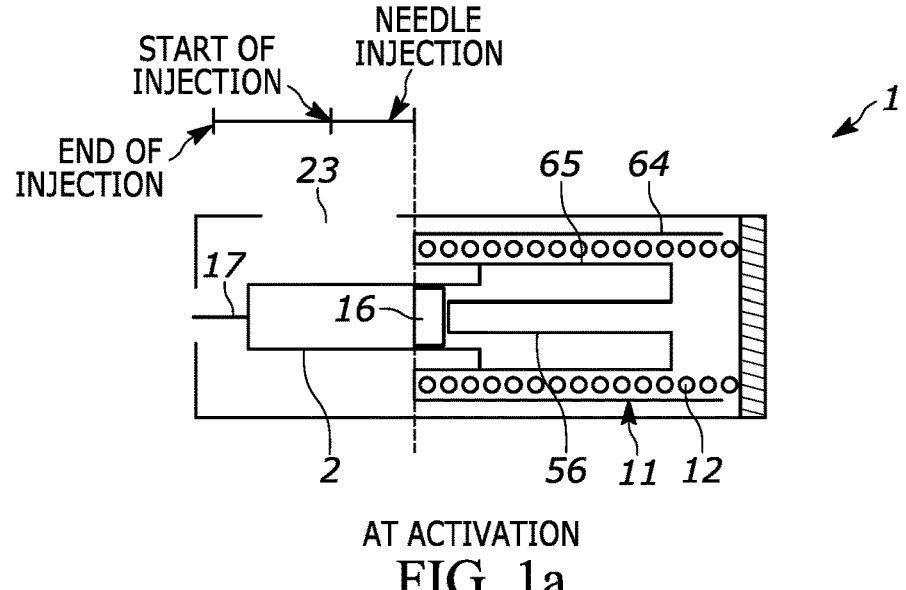
AT ACTIVATION
FIG. 1a
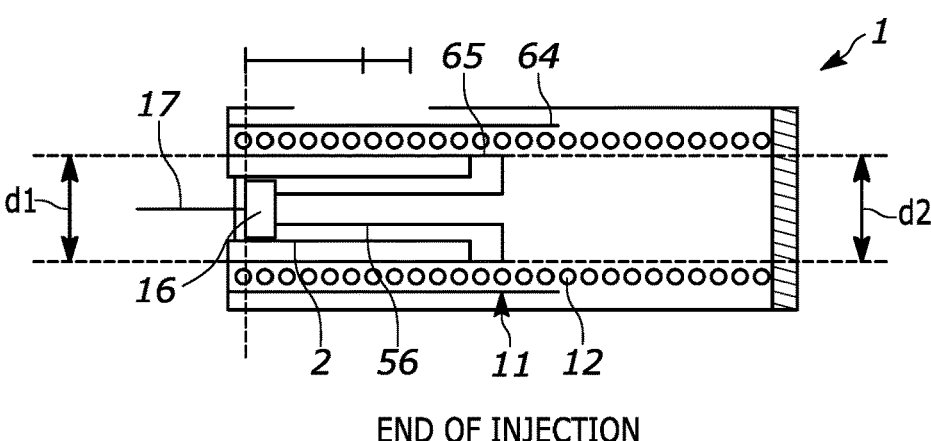
AFTER NEEDLE INSERTION
FIG. 1b
END OF INJECTION
FIG. 1c

| NEEDLE GAUGE | FOR IT<5 s | FOR IT<7 s | FOR IT<10 s |
|---|---|---|---|
| 31G RW | 5 cP | 8 cP | 12 cP |
| 30G RW | 10 cP | 16 cP | 23 cP |
| 29G RW | 19 cP | 28 cP | 41 cP |
| 27G RW | 33 cP | 47 cP | 69 cP |
| 27G TW | 78 cP | >100 cP | >100 cP |
| 27G XTW | >100 cP | >100 cP | >100 cP |

DRUG DELIVERY DEVICE

CROSS-REFERENCE TO RELATED APPLICATION

This is the United States national phase of International Patent Application No. PCT/US2020/054496, filed Oct. 7, 2020, which claims the priority benefit of U.S. Provisional Application No. 62/912,316, filed Oct. 8, 2019, entitled "Drug Delivery Device, the entire contents of each of which are incorporated by reference herein.

FIELD OF DISCLOSURE

The present disclosure relates to drug delivery devices. More particularly, the present disclosure relates to a device for injecting a liquid medicament having a drive mechanism.

BACKGROUND

Compressed springs are often the preferred choice for providing the required injection drive force in pen shape autoinjectors because of their low cost and convenient manufacturing. However, the maximum force and power that a spring can deliver in an autoinjector is limited due to several design constraints.

To keep the device length within a comfortable range for patients, almost in all spring driven pen injectors, the compressed spring decompresses into the syringe during the injection. While this enables reducing the device length (for example, by a couple of inches), it limits the spring outer diameter significantly. Consequently, the maximum force that typically can be generated by the spring is limited considering that the maximum stress within the spring wire generally cannot exceed the yielding stress of the spring material.

The present disclosure sets forth drug delivery devices embodying advantageous alternatives to existing drug delivery devices, and that may address one or more of the challenges or needs mentioned herein.

SUMMARY

An aspect of the present disclosure provides a drug delivery device including a housing having an opening, a drug storage container, a plunger rod, and a drive mechanism. The drug storage container may have an inner surface at least partially defining a drug storage chamber and an outer surface defining an outer diameter. The drug storage container may further include a plunger stopper and a delivery member having an insertion end configured to extend at least partially through the opening during a delivery state. The drive mechanism may be activatable to drive the plunger stopper in a distal direction to expel a drug from the drug storage container through the delivery member. The drive mechanism may have an inner surface with an inner diameter greater than the outer diameter of the outer surface of the drug storage container.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

FIGS. 1a-1c are schematic views of a drug delivery device according to an embodiment of the present disclosure, in various stages of an injection process.

DETAILED DESCRIPTION

Figure 2:
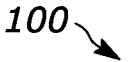
FIG. 2 is a side view of a drug delivery device according to an embodiment of the present disclosure, with some components being transparent for illustrative purposes.
Figure 2:
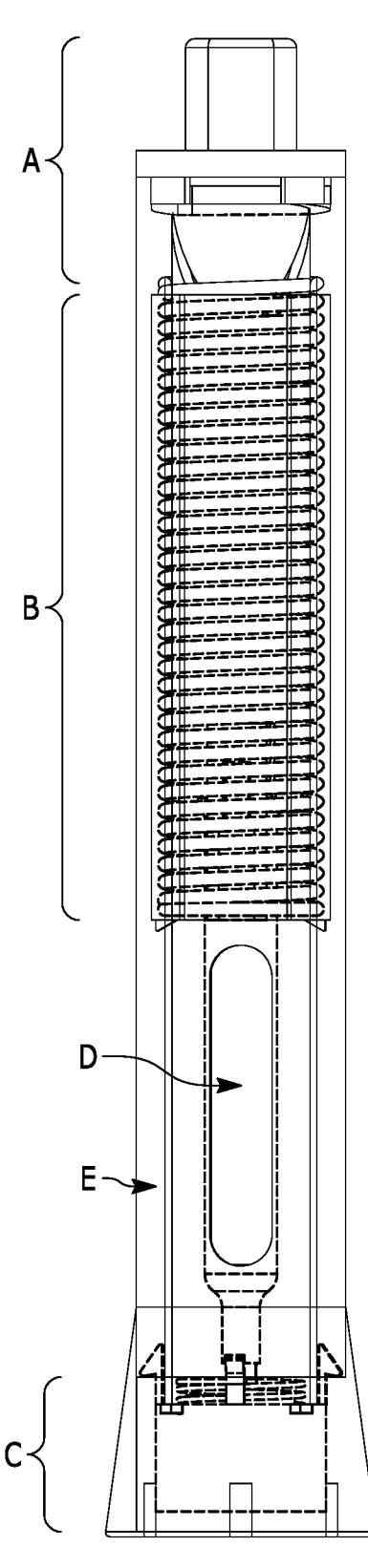

The present disclosure generally relates to drug delivery devices operable by a user for administering a drug, or in the case where a patient is the user, self-administering a drug. Various features are disclosed to facilitate an improved drive mechanism for the drug delivery device, such as a drive mechanism for injecting the medicament into a patient. The improved drive mechanism permits the drug delivery device to generate, and the components thereof to tolerate, larger injection forces than those typically generated and tolerated by known drug delivery devices. For example, in one embodiment the drug delivery device utilizes a spring drive that has an inner diameter larger than the outer diameter of the syringe barrel. As another example, in one embodiment the drug delivery device utilizes a spring drive that decompresses to extend over the syringe barrel (rather than within the syringe barrel). As yet another example, in one embodiment the drug delivery device utilizes a force transmitter component to transfer force from the drive spring to the plunger stopper of the syringe.

The improved design drive mechanism offers many advantages over known delivery devices, such as: having a shorter overall length (e.g., an overall axial length) for the drug delivery device, permitting the delivery of drugs having a relatively high viscosity, reducing the likelihood of breakage of syringe components, utilizing the outer surface of the spring to signal to the user the stage of the injection (while also having the option of concealing the drive spring with an outer sleeve of the force transmitter component should that be desirable), and minimizing lateral deformation of the spring (e.g. buckling and other deformations).

The improved drive mechanism features disclosed herein leverage the actuation of other components included in a drug delivery device, and, as such, do not add undue complexity to the design or manufacture of the drug delivery device. These and other advantages will be apparent to one of ordinary skill in the art reviewing the present disclosure.

FIGS. 1a-7e illustrate several views of embodiments of a drug delivery device for delivering a drug, which may also be referred to herein as a medicament or drug product. The drug may be, but is not limited to, various biologicals such as peptides, peptibodies, or antibodies. The drug may be in a fluid or liquid form, although the disclosure is not limited to a particular state. In certain liquid formulations, the drug may have a viscosity between approximately (e.g., ±10%) 1-13 centipoise (cP), between approximately (e.g., ±10%) 1-30 cP, between approximately (e.g., ±10%) 1-60 cP, between approximately (e.g., ±10%) 1-90 cP, or higher or lower viscosities.

Various implementations and configurations of the drug delivery device are possible. The present embodiment of the drug delivery device is configured as a single-use, disposable injector. In other embodiments, the drug delivery device may be configured as multiple-use reusable injector. The drug delivery device is operable for self-administration by a patient or for administration by caregiver or a formally trained healthcare provider (e.g., a doctor or nurse). The present embodiment of the drug delivery device takes the form of an autoinjector or pen-type injector, and, as such, may be held in the hand of the user over the duration of drug delivery or dosing. The drug delivery device may alternatively be a wearable (a.k.a. on-body or ambulatory) drug delivery device.

The configuration of various components included in the drug delivery device may depend on the operational state of the drug delivery device. As shown in FIGS. 1a-1c, the drug delivery device 1 may have a pre-delivery or storage state, a delivery or dosing state, and a post-delivery state, although fewer or more states are possible. The pre-delivery state may correspond to the configuration of the drug delivery device 1 subsequent to assembly and prior to activation by the user. In some embodiments, the pre-delivery state may exist in the time between when the drug delivery device leaves a manufacturing facility and when a patient or user activates a drive of the drug delivery device 1. This includes the moments in time after the user has removed the drug delivery device from any secondary packaging and prior to positioning the drug delivery device against the injection site. The delivery state may correspond to the configuration of the drug delivery device while drug delivery is in progress. The post-delivery state may correspond to the configuration of the drug delivery device after drug delivery is complete and/or when the plunger stopper is arranged in an end-of-dose position in a drug storage container.

The drug delivery device may include an outer casing or housing. In some embodiments, the housing may be sized and dimensioned to enable a person to grasp the injector in a single hand. The housing may have a generally elongate shape, such as a cylindrical shape, and extend along a longitudinal axis between a proximal end and a distal end. An opening may be formed in the distal end to permit an insertion end of a delivery member to extend outside of the housing. A transparent or semi-transparent inspection window 23 may be positioned in a wall of the housing to permit a user to view component(s) inside the drug delivery device, including a drug storage container. Viewing the drug storage container through the window may allow a user to confirm that drug delivery is in progress and/or complete. A removable cap may cover the opening prior to use of the drug delivery device, and, in some embodiments, may including a gripper configured to assist with removing a sterile barrier (e.g., a rigid needle shield (RNS), a flexible needle shield (FNS), etc.) mounted on the insertion end of the delivery member such as, for example, needle 17. The gripper may include one or more inwardly protruding barbs or arms that frictionally or otherwise mechanically engage the sterile barrier to pull the sterile barrier with the removable cap when the user separates the removable cap from the housing. Thus, removing the removable cap has the effect of removing the sterile barrier from the delivery member.

Referring to one exemplary embodiment in FIGS. 1a-1c, a general overview of a drug delivery device is as follows. The inner surface of the spring 12 has an inner diameter d1 that is greater diameter than an outer diameter d2 of the outer surface of the drug storage container 2, more specifically the syringe barrel, such that upon decompression the spring 12 extends forward (e.g., in the distal direction) while being annularly located outside of the syringe barrel. During this movement, the spring 12 depresses the plunger stopper 16 via a coupling piece (i.e., a force transmitter). The force transmitter 11 shown in FIGS. 1a-1c has a drive rod 56 in its center and two cylindrical shells: an inner shell 65 and an outer shell 64. The inner shell 65 and the outer shell 64 may be coaxial with the rod 56. As the result, two cylindrical or annular gaps exist within the force transmitter piece: an outer gap and an inner gap. The outer gap is located radially between the outer shell 64 and inner shells 65. The outer gap is closed at the syringe engaging end and is open at the spring engaging end. The drive spring 12 resides within the outer gap. The inner gap is located radially between the drive rod 56 and the inner shell 65; it is open at the syringe engaging end and closed at the spring engaging end. The syringe slides within the inner gap. The drive rod 56 contacts the plunger stopper 16 of the syringe during the needle insertion and injection administration.

Releasing the initially compressed spring 12 causes the force transmitter 11 to contact the plunger stopper 16; it initially moves the syringe toward a hard stop (causing the needle insertion) and then moves the plunger stopper 16 with respect to syringe to administer the injection (FIG. 1b-1c).

Referring now to FIG. 2, another embodiment of a drug delivery device 100 will be described in more detail, by subassembly components. The disclosed drug delivery device 100, which may be an autoinjector system in some embodiments, includes of five major subassemblies. Subassembly A, the activation subassembly, activates the device in when an activation force of certain magnitude is applied to it by the user.

Subassembly B, the drive subassembly, provides the required drive force for needle insertion and for the injection of liquid medicament. Subassembly B uses stored energy of a compressed helical spring as the source of force generation. Subassembly B and subassembly A are engaged together to keep the spring at the compressed state prior to use. During activation subassembly A disengages from subassembly B and releases the compressed spring.

Subassembly C, the needle cover subassembly, covers the needle after completion of injection and removal of the device from the body. At the completion of injection, subassembly B engages with subassembly C and releases the needle cover. In some embodiments the drive force for ejecting the needle cover is provided by the injection drive subassembly (subassembly B), and in some embodiments it is generated by a separate drive mechanism that is a part of subassembly C.

Subassembly D is the syringe subassembly and it may incudes a syringe prefilled with the liquid medicament, microbially sealed by a needle shied at the needle end, and a plunger stopper at the other end. After device activation, subassembly B engages with subassembly D to transfers the drive force of subassembly B to subassembly D. In some embodiments, the same drive force is transferred to one or multiple locations of subassembly D both to move the syringe for needle insertion and to move the plunger stopper for liquid medicament administration. In some embodiments, the required force for needle insertion and for liquid medicament administration are separate and/or generated by separate mechanisms. Subassembly D may alternatively utilize any other suitable primary container for holding the medicament, such as a pre-filled cartridge, a user-filled syringe or cartridge, or other suitable component(s).

Subassembly 5 is the device housing. Subassembly E provides mechanical support for different elements and subassemblies of the device and protects the inner elements and subassemblies from external forces and energies. It may engage and disengage with different elements and subassemblies at different phases of the device function.

FIGS. 3a-3d collectively show an exploded view of the device housing subassembly for a drug delivery device according to an embodiment of the present disclosure. For example, device housing 105, includes three parts: housing body 107, housing bottom 108, and housing cap 109. Housing body 107 provides support for drive subassembly B, and activation subassembly A. Housing body 107 has a window 123 that is along all or part of the syringe subassembly D and enables full or partial view of the syringe subassembly C, and its drug product content (not shown). Housing body 107 has some body lower connecting features 125, at its lower end, for connection to the housing bottom 108. These are connected to their conjugate parts, the housing bottom connecting features 126, in the housing bottom 108. Housing body 107 include some axial slots 127 on its inner surface that couple with axial ribs 128 on the outer surface of the force transmitter 111. There is a clearance between the axial ribs 128, and axial slots 127, that is filled with a viscous material 129 like silicon oil or other suitable lubricant(s). The combinations of axial slots 127 and axial ribs 128, not only constrains the movement of force transmitter 111 to axial direction but also along with the viscous material 129 form a damping mechanism for the device.

Figures 3A, 3B, 3C:
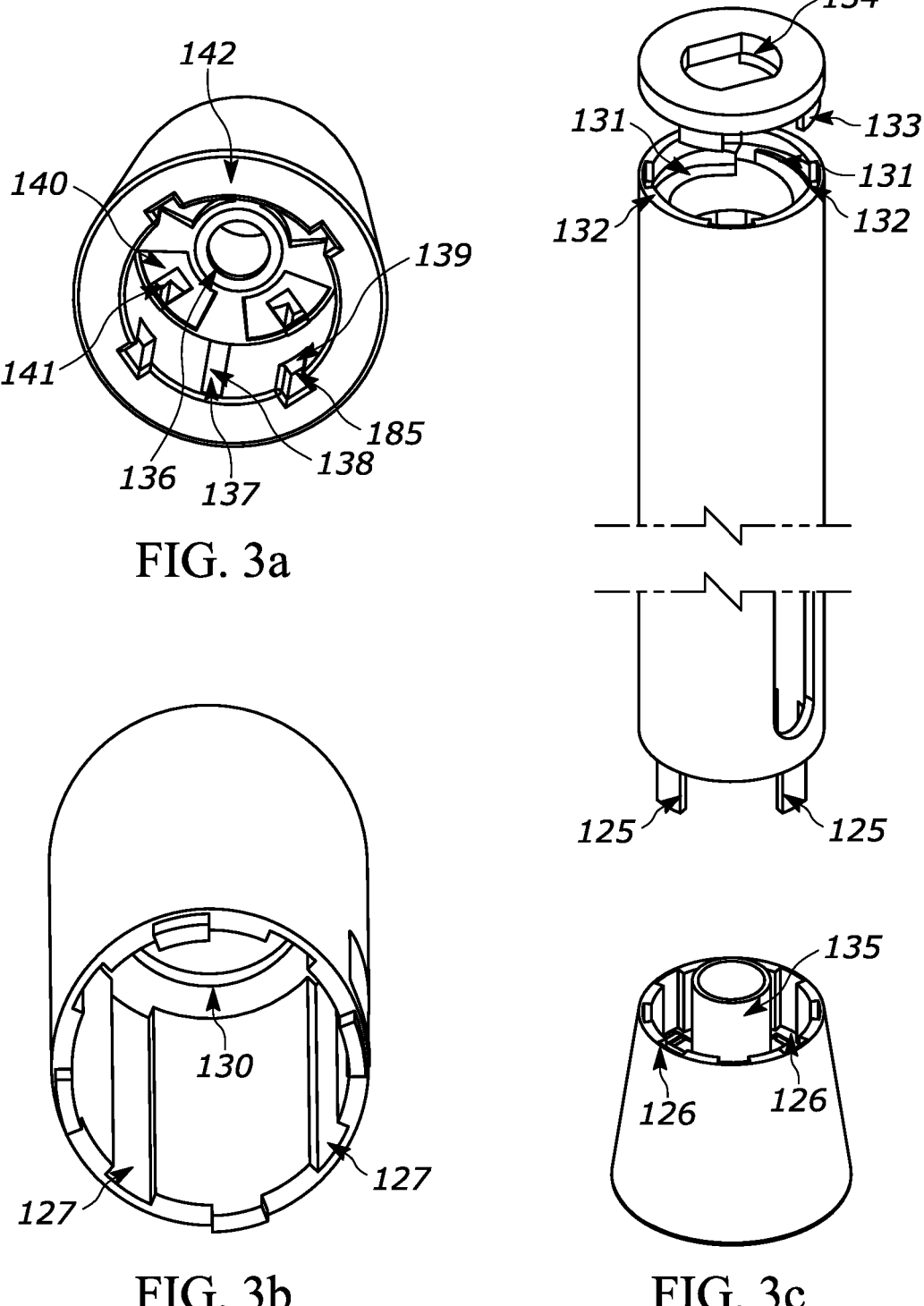
FIGS. 3a-3d collectively show an exploded view of the device housing subassembly for a drug delivery device according to an embodiment of the present disclosure.
Figure 3D:
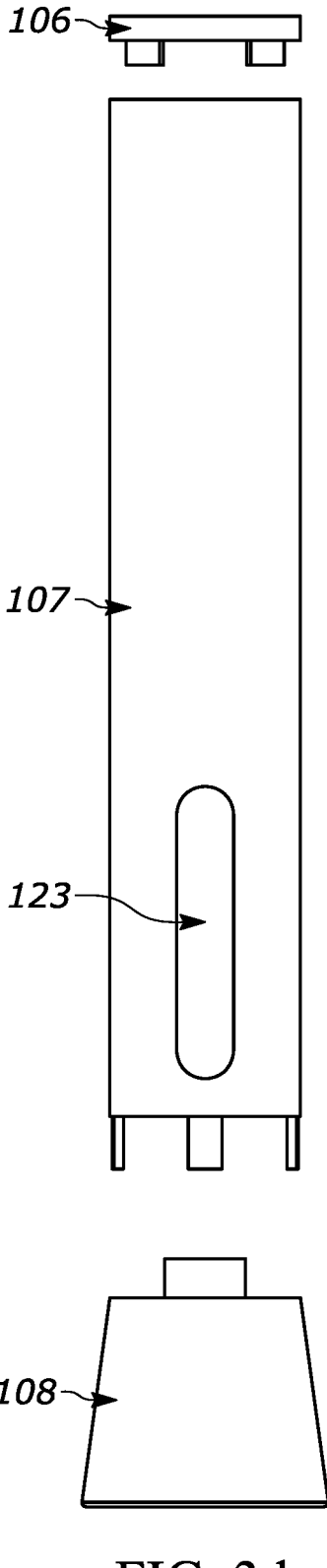

On the inner surface of the housing body 107, toward the upper end, there is a circular support extrusion 130, as seen in FIG. 3b. Drive spring 112 resides against the lower surface of the circular support extrusion 130. Portions or all the upper surface of the circular support extrusion 130 forms the release core seat 131. The surface of the release core seat 131 may be flat or may be inclined and form a partial helix. It may include of 2 or more similar segments. At the upper end of the housing body there are the body upper connecting features 132, that are coupled with their conjugate cap connecting features 133, on the housing cap 106. Housing cap 106, has a cap button cut 134, that is similar to the non-circular cross section of the activation button 109, and enables the housing cap 106, to slide over the activation button 109, during the assembly. The cap button cut 134 may constrain the movement of the activation button 9 in the axial direction.

The housing bottom 108 shown in the figures is formed as a cylindrical, conical or any other shell. It has a flexible disk 140, that separates its inner volume of the shell into an upper volume 143, and a lower volume 144. The needle cover subassembly C, is located in the lower volume 144. The lower end of the force transmitter 111, resides in the upper volume at the completion of injection. In some embodiments the flexible disc is located at the top of the housing bottom 108, eliminating the upper volume. In the middle of the flexible disk 140, there is the syringe radial support 135, which is an extruded upward open-ended shell that covers the surrounding of the barrel 115 at its tip (needle end) and support the barrel 115, laterally at its tip during the needle insertion and injection. The barrel 115 is also supported axially by syringe axial support 136, which is an inward circular extrusion on the inner surface of the syringe radial support 135. Flexible disk 140 may deflect downward when barrel 115 pushes against the syringe axial support 136.

Flexible disk openings 141, are openings within the flexible disk 140, to allow the needle cover release cantilevers 145, the needle cover release hooks 176, needle cover backstop cantilevers 146, and needle cover backstops 180, to pass though the flexible disk 140 from the lower volume 144, to the upper volume 143. Needle cover grooves 138, are axial slots in the inner surface of the lover volume and are engaged with the needle cover guide 147 to constrain the movement of the needle cover cup 120, in the axial direction. The flat surface at the end of the needle cover groove 138 is the needle cover forward stops 137; once it is engaged with the needle cover guide 147, it stops further forward movement of the needle cover cup 120. The lower surface of the housing bottom 18, forms the housing patient contact 142. There are slots starting from this surface. The surface at the other end of these slots are the needle cover backstop supports 139, that once engaged with the needle cover backstops 180 at the completion of needle cover ejection, prevent the backward movement of the ejected needle cover cup 120. Needle cover backstop supports 139 may be flat (e.g., horizontal) or inclined.

Figure 4B:
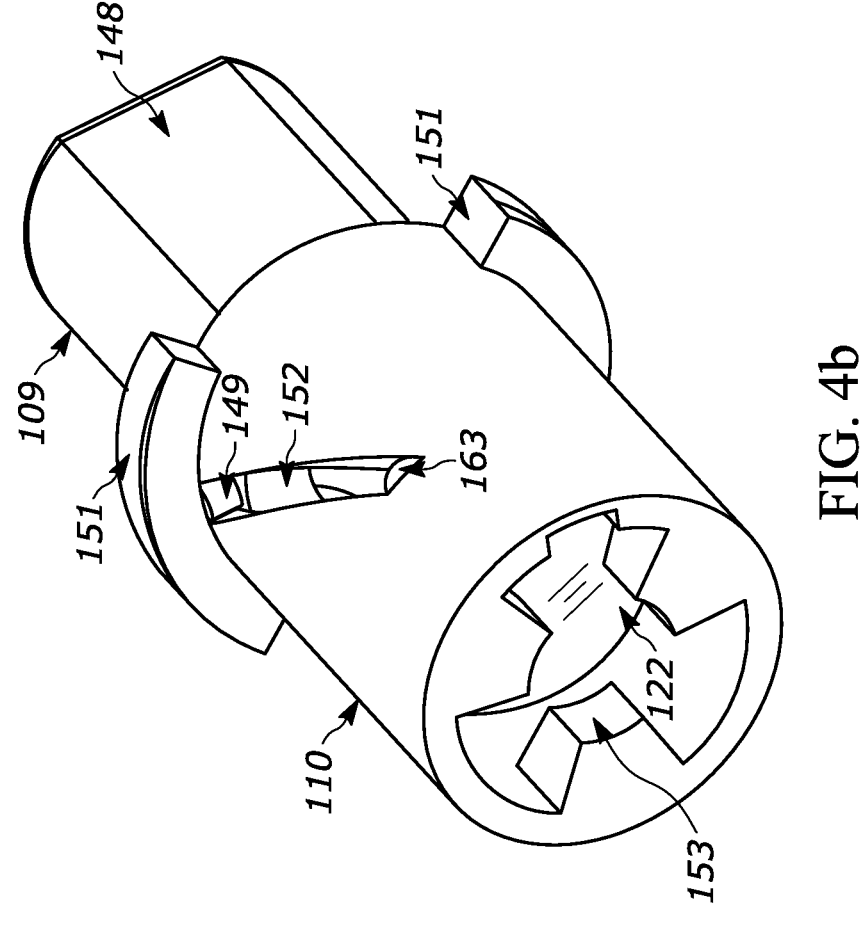
FIG. 4b shows an isometric view of the activation subassembly for a drug delivery device according to an embodiment of the present disclosure.
Figure 4A:
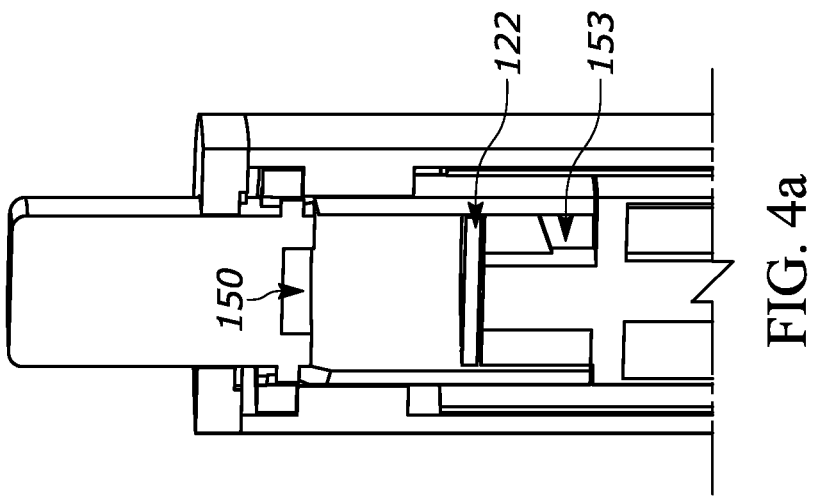
FIG. 4a shows a partial cross-sectional view of the activation subassembly for a drug delivery device according to an embodiment of the present disclosure.
Figures 5A, 5B, 5C, 5D:
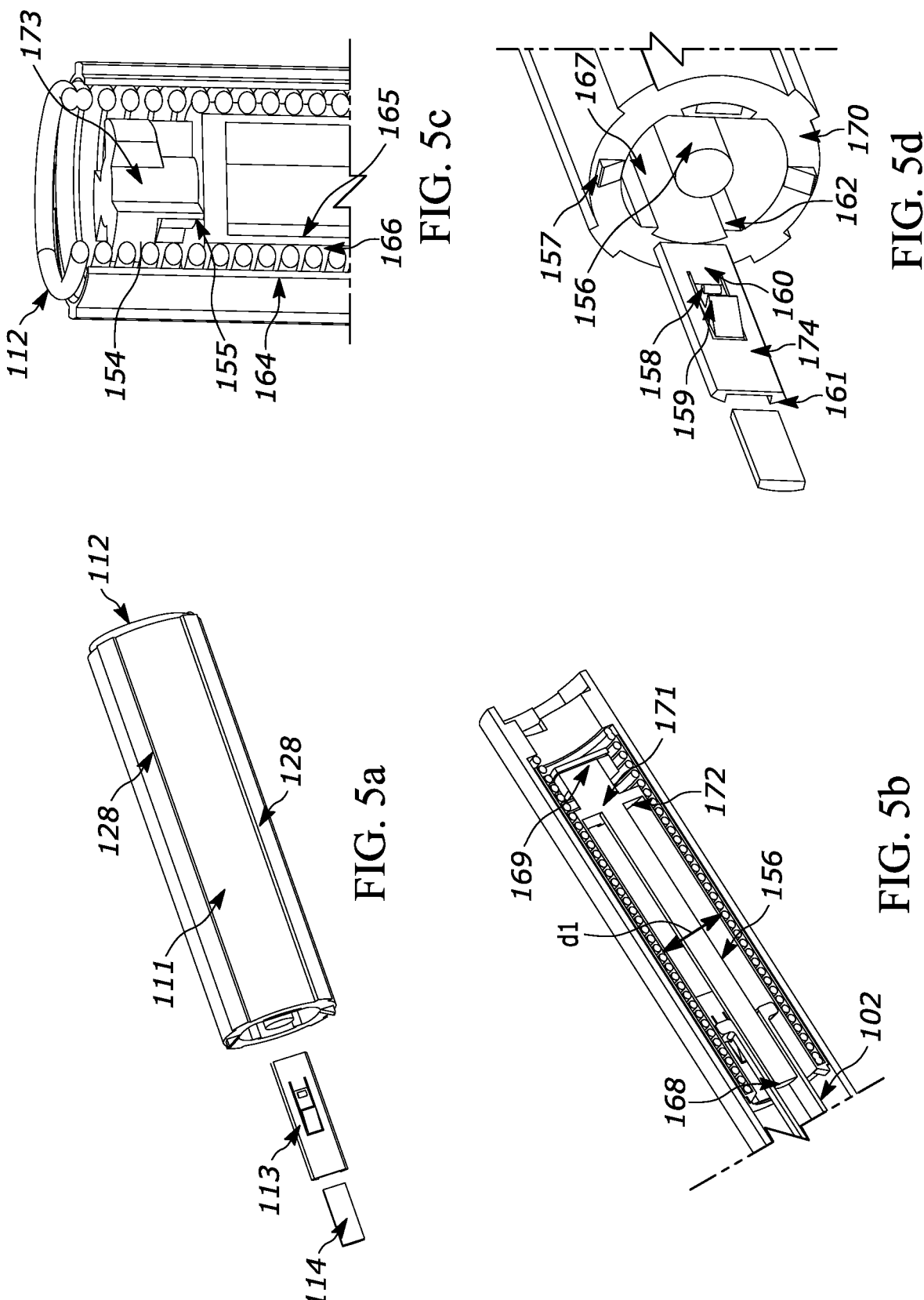
FIGS. 5a-5d show various views of different aspects of the drive subassembly for a drug delivery device according to an embodiment of the present disclosure.

FIG. 4a shows a partial cross-sectional view of the activation subassembly for a drug delivery device according to an embodiment of the present disclosure. Activation subassembly A, includes of two parts: activation button 109 and release core 110. In some embodiments, it also includes: button spring and button spring pad 122. Activation button 109 has a cylindrical shape including anti-rotation features 148. In some embodiments, the anti-rotation features 148 are flat surface resulted from axial cuts on the sides of the button. The cross section of the activation button 109 matches the cap button cut 134. Activation button has a button spring seat 150, at one end that provides support for the upper end of the button spring 121 (for those embodiments with button spring 121). Activation button has two (or more) button pins 149 at its outer surface that are inserted into the helical grooves 152 of the release core 110. Release core 110 is a cylindrical shell that has two or more outward hanging supports 151 at one end and three or more inward release hooks 153 at the other end. The lower surface of the hanging supports 151 may be flat or inclined, and seats against the release core seats 131 with similar surface. Release core 110 has two or more helical grooves 152, that start from its upper surface. The initial part of the helical grooves 152 may be axial or a partial helix. The release hooks 153 are inward extrusions on the inner surface of the release core at one end; their upper and lower surface may be flat or inclined. The upper surface of the release hooks 153 engages with the lower surface of the hold hooks 154 of the force transmitter 111, and should match for a proper contact. Button spring pad 122 is a flat disk with two or more button spring pad pins 163 extruding radially at its perimeter. Button spring pad pins 163 are placed into the helical grooves 152 and will be secured to the bottom end of the helical grooves 152. The upper surface of the button spring pad 122 provides the support for the lower end of the button spring 121, if included.

Activation Dynamics:

In the embodiment shown in FIGS. 4a and 4b, in order to activate the device, user pushes the activation button 109. As the result the button pins 149 engage with helical groves 152. The reaction force at the contact, applies rotating moments to both release core 110 and activation button 109. The anti-rotation features 148 of the activation button 109, engages with its conjugate on the housing cap 106, the cap button cut 134. As the housing cap 6 is secured to the housing body 107 via the cap connecting features 133 and body upper connecting features 132, the activation button 109 cannot rotate; the additional moment caused by the engagement of the activation button 109 and housing cap 106 cancels the moment of reaction force between the button pins 149 and helical groves 152. In contrast, rotation of release core is not constrained and if the activation force of the upper surface of the activation button 109 is sufficiently large to overcome all the frictional moments, the release core 110 will rotate. The inclination angle of the lower surface of the hanging support 151, would be used to adjust the activation force by generation a supplementary activation moment from the axial force of the drive spring 112 that is transferred to this contact.

As the activation button 109 moves downward, the release core rotates, transferring a force and so a moment to the force transmitter 111, via the contact between the release hooks 153 and hold hooks 154. As the rotation of force transmitter piece is prevented buy the engagement of housing body axial slots 127 and force transmitter axial ribs, the release hooks 153 slide rotationally over the hold hooks until there is no contact between them. At this moment the device is activated, the force transmitter 111 has no axial support and starts to move downward axially.

However, the principles of the embodiments described herein may be utilized without an activation button, such as a drug delivery device that is activated by movement and/or position of the needle shield rather than (or in addition to) depressing an activation button.

FIGS. 5a-5d show various views of different aspects of the drive subassembly for a drug delivery device according to an embodiment of the present disclosure. Drive subassembly B includes the: force transmitter 111, drive spring 112 and syringe holder 113. In some embodiments the syringe 102 or other drug storage container is locked in the syringe holder 113 upon its assembly into the device, and in some embodiments a syringe lock pin 114 is required to lock the syringe 102 into the device after its assembly. Force transmitter 111 has a plunger rod 156 in its center, a force transmitter inner shell 165, and a force transmitter outer shell 164, coaxial together. As the result, there is a force transmitter spring cavity 166, between the force transmitter inner shell 165, and the force transmitter outer shell 164, and a force transmitter syringe cavity 167, between the plunger rod 56 and the force transmitter inner shell 165. Force transmitter distal end 168 is the end that is engaged with syringe subassembly D; and force transmitter proximal end 169 is the end that is engaged with the activation subassembly A.

The force transmitter spring cavity 166 is closed at a force transmitter distal end 168 by a surface called force transmitter spring support 170. The force transmitter spring cavity 166 is open at a force transmitter proximal end 169. At least the distal end of the drive spring 112 resides within the force transmitter spring cavity 166. The force transmitter syringe cavity 167 is open at the force transmitter distal end 168. The force transmitter syringe cavity 167 is closed at a force transmitter proximal end 169 by the force transmitter hold feature 171. The syringe 102 slides within the force transmitter syringe cavity 167, at least during assembly.

Force transmitter hold feature 171, includes of a base plate 172, three or more hold hooks 154, a hold hook support 173, and a release hook stop 155, for each release hook 153. Note the number of release hooks 153 and hold hooks 154 are the same as each release hook 153 is engaged with one hold hook 154. During assembly, the release core 110, is inserted into the force transmitter hold feature 171, by aligning the release hooks 153, with the spaces between the hold hooks 154. After insertion, the release core 110, rotates until the release hooks 153 reside against the release hook stops 155. During this process (which may involve insertion and rotation) the force transmitter 111, is supported externally. After this process the external support can be removed to allow the release hooks 153 to engage the hold hooks 154.

Syringe holder 113 is a piece that is inserted in and secured to the force transmitter 111, between the syringe holder supports 162. the syringe holder 113 contains features to secure the syringe subassembly D to the force transmitter 111. In some embodiments these features can be added to the force transmitter 111 directly. Syringe holder 113 includes a syringe holder base plate 174, a syringe holder locking groove 161 that is a cut in the outer surface of the base plate 174, and a syringe holder cantilever 160, that is located within and connected to the base plate 174. Syringe holder cantilever 160 contains a syringe holder hook 159 at the free end, and syringe driver pin 158 in the middle. Syringe holder hook 159 has an inclined surface that engages with barrel flange 175 during the insertion of the syringe into the device. As the result, the syringe holder cantilever 160, deflects and the syringe holder hook 159 moves out of the away of syringe, allowing the syringe subassembly D to be inserted into the force transmitter 111. Once the barrel flange 175 passed beyond the syringe holder hook 159, the syringe holder cantilever 160 deflects back toward its undeformed state, placing the syringe holder hook 159 underneath the barrel flange 175. In some embodiments the syringe holder cantilever 160 and the syringe holder hook 159 are designed so that the syringe holder hook 159 is locked underneath the barrel flange 175 and prevents the downward motion of the barrel. In some embodiments a syringe lock pin 114 is inserted into the syringe holder locking groove 161, to prevent outward deflection of the syringe holder cantilever 160 and so locks the downward motion of the syringe 102. The upward or proximal motion of the syringe 102 is constrained by the syringe drive pin 158. The syringe drive pin 158 can move away from the path of the barrel flange 175 in response to a sufficiently large axial force, by deflecting the syringe holder cantilever 160.

Needle cover releasers 157 are two or more extrusions on the outer surface of force transmitter spring support 170. Once the force transmitter approaches its end of travel, the needle cover releasers 157 engage with the needle cover release hooks 176 to release the needle cover 120.

Needle Shield Removal:

To prepare the device for injection, the needle shield 118 is typically removed to gain access to the needle 117 (although the needle is still typically annularly surrounded by the needle shield at this point). The applied axial force on the needle shield 118 that is required for needle shield removal, is transferred to the barrel 115, and then to the syringe holder hooks 159. Combinations of syringe holder hooks 159, syringe holder cantilever 160, syringe holder base plate 174, syringe holder locking grooves 161, and syringe lock pins 114 (for those embodiments that include them), is designed so that syringe holder 113 keeps the syringe 102 inside the force transmitter 111 for a maximum axial force acting on the needle shield 118. Some minor deflection of deformation may be expected.

Plunger Rod to Plunger Stopper Impact:

Once the device is activated and the force transmitter 111 is released, then the force transmitter 111 accelerates and moves axially under the net force of compressed spring. There would a viscous friction (which in some embodiments may be proportional to the force transmitter velocity) at the lubricated contacts between the force transmitter axial ribs 128 and housing body axial slots 127. This damping mechanism limits the maximum velocity of the force transmitter 111. At certain point the plunger rod 156 of the force transmitter 111, impacts the plunger stopper 116, of the syringe subassembly D. The impact magnitude can be controlled by adjusting the length and width of, and the clearance between, the force transmitter axial ribs 128 and their conjugate housing body axial slots 127, and by selecting with different viscous materials 129 with different viscosities. After the impact the plunger stopper 116, moves with the force transmitter 111.

FIGS. 6a-6d shows various views of different aspects of the syringe subassembly D for a drug delivery device according to an embodiment of the present disclosure. Syringe subassembly D, includes a barrel 115, a plunger stopper 116, a needle 117 and a needle shield (not shown in FIGS. 6a-6d). In some embodiment needle is integral to the barrel and in some embodiments is attached via a connector (e.g., a Luer connector). Toward the syringe end, the barrel diameter reduces forming a barrel shoulder 182. At the open end of the barrel 115, there is a barrel flange 175 that is usually used as a support for holding the barrel 115. Prior to activation, the syringe subassembly D is constrained in all displacement and rotation directions. The axial movement is constrained by syringe holder hooks 160 and syringe drive pins 158. The lateral movement is constrained at both ends: at barrel flange by the force transmitter inner shell 165, the plunger rod 156, and syringe holder 113, and at needle end by syringe radial support 135. The rotation about axis is constrained by the contact between the noncircular cross section of barrel flange 175 and force transmitter inner shell 165.

Needle Insertion and Partial Retraction Dynamics:

Following the release of force transmitter 111, the syringe drive pins 158 engage with the barrel flange 175 and transfer a portion of the drive force to barrel flange 175. If the transferred force is less than the required force to deflect the syringe holder cantilever 160 and disengage the syringe drive pins 158 away from the barrel flange 175, the syringe drive pins 158 stay engaged with barrel flange 175 and drive the syringe and so the needle in the downward or distal direction. After release of force transmitter 111, if the transferred force by the syringe drive pins 158 to the barrel flange 175 is greater than the required force to deflect the syringe holder cantilever 160 and disengage the syringe drive pins 158, the syringe drive pins 158 disengage from barrel flange 175 after a short period of engagement and a limited movement of syringe. Following disengagement of the drive pins 158 from barrel flange 175, the plunger rod 156 impacts to the plunger stopper 116. Following this impact, the barrel 115 along with the drug product 124, move downward by the force transmitter 111 motion. The syringe radial support 135, prevents any probable lateral movement of the barrel.

Downward motion of the syringe 102 causes the needle 117 to extend axially outside the needle cover patient contact 181, and being inserted into the body if the device is placed against the body. The downward motion of the barrel 115 is stopped by the impact between the barrel shoulder 182 and the syringe axial support 136 located at the center of flexible disk 140. The impact duration and so the peak impact force can be adjusted by adjusting the flexibility of the flexible disk 140. Also, the flexibility of the flexible disk and the damping mechanism parameters can be adjusted to impose a partial retraction of the needle by making imposing a limited upward or proximal motion of barrel 115 (and underdamped system). The partial retraction helps to reduce the tissue resistive pressure during the injection.

Injection Dynamics:

Once the downward motion of the barrel 115 is stopped by the impact between the barrel 115 and housing bottom 108, and the barrel shoulder 182 is rested against the inner edge of the syringe axial support 136, any probable engagement between the syringe drive pins 158 and the barrel flange 175 is released. The force transmitter 111 and the plunger stopper 116 continue their downward (e.g., distal) motion (which in some embodiment may be at a much slower rate as compared to their initial movement), extruding the liquid medicament out of the barrel 115 and needle 117. This process continues until plunger stopper 116 reaches the end of the barrel 115 and the resultant reaction force at the barrel 115 to plunger stopper 116 contact cancels the net drive force.

FIGS. 7a-7e show various views of different aspects of the needle cover subassembly C for a drug delivery device according to an embodiment of the present disclosure. Needle cover subassembly C, includes of a needle cover cup 120, and a needle cover spring 119. Needle cover cup 120 includes two coaxial cylindrical shells, the needle cover inner shell 183 and the needle cover outer shell 184 that is open at one end and closed by the needle cover patient contact 181 at the other end. At the center of the needle cover patient contact 181, there is the needle shield removal opening 179, that provide access to the needle shield 118 for its removal prior to injection. Between the needle cover inner shell 183 and needle cover outer shell 184 is the needle cover spring cavity 178, where the needle cover spring 119 resides. Compressed needle cover spring 119 is supported at on end by the inner surface of the needle cover patient contact 181 and at the other end by the flexible disk 140.

On the upper edge of the outer shell there are 103 distinct types of extrusions. First one is the needle cover release cantilever 145 which is an axial extrusion connected to the needle cover release hook 176. The second one is the needle cover backstop cantilever 146, that is also an axial extrusion attached to the needle cover backstop 180. The third one is the needle cover guide 147 which is a radial extrusion. There are two or more of each extrusion type in the needle cover cup 120.

Prior to activation, the lower surface of the needle cover release hooks 176, seats against its conjugate surface, the needle cover release seats 177 of the housing bottom 108. The contact surfaces may be flat or inclined. The upper surface of the needle cover release hooks 176 is inclined to transform the axial movement of the needle cover releasers 157, after contacting the needle cover release hooks 176, to the lateral movement of the needle cover release hooks 176. The lower surface of the needle cover backstops 180 is inclined so that once contacted the flexible disk 140 during the ejection of the needle cover cup 120, its axial movement also causes an inward lateral movement and bending the needle cover backstop cantilever 146. The upper surface of the needle cover stops 180 may be flat or inclined. Needle cover guide 147 are coupled into the needle cover grooves 138 of the housing bottom 108 with some clearance and so can move in axial direction without any significant frictions.

Needle Cover Release Dynamics:

Toward the end of injection, the downward motion of the force transmitter 111, bring into contact the needle cover releasers 157 and the needle cover release hooks 176. Because of inclined lower surface of the needle cover releasers 157 and upper surface of needle cover release hooks 176 the downward motion of the needle cover releasers 157 applies a lateral inward force to the needle cover release hooks 176 which, if is sufficient, overcomes the resistive forces and moves the needle cover release hooks 176 inward, up to the point that it is no longer in contact with needle cover release seats 177. This eliminates the normal reaction force at the contact between needle cover release seats 177 and needle cover release hooks 176 that was cancelling the axial force of the compressed needle cover spring 119. At this point the needle cover ejection is activated and the force of the compressed needle cover spring 119 moves the needle cover cup 120 outward. The interaction between the needle cover guide 147 and needle cover grooves 138 keeps the ejection motion of the needle cup 120 aligned in the axial direction.

Haptic and Audible EOD Signals Generation:

At the instance that the needle cover release hooks 176 are released the needle cover release cantilever 145 is deflected inward and the needle cover release hook 176 is detached from the upper surface of the needle cover release seats 177. Under the influence of the force of the needle cover spring 119, the needle cover release hooks 176 move below the flexible disk 140. Once the Needle cover release hooks 176 become disengage from the flexible disk 140, there would be no lateral force acting on them and the needle cover release cantilevers 145 comes back to the vertical position, impacting the inner surface of the housing bottom. This impact generates an audible signal for the end of delivery.

During the downward motion of the needle cover cup 120, the inclined contact between the lower surface of the needle cover backstop 180 and flexible disk 140 and the extension of needle cover backstop 180 outside the perimeter of its flexible disk opening 141, causes the needle cover backstop cantilever 146 to bend inward during the passing of the needle cover backstop 180 through the flexible disk 140. Once the needle cover backstop 180 disengaged from the flexible disk, the needle cover backstop cantilever 146 straighten back again casing the needle cover backstop 180 to impact the inner surface of the housing bottom 108. This impact generates another audible signal that may occur about the same time shortly after or shortly before the previously explained audible signal. Needle cover backstop 180 also extends outside the perimeter of the inner surface of the housing bottom 108.

Dimensions of the needle cover backstop cantilever 146, needle cover backstop 180, needle cover release hooks 176, and needle cover release cantilevers 145 can be adjusted to change the timing and strength of these two audible signals.

Once the needle cover cup is released at the completion of injection, the force of the needle cover spring 119 is transferred to the needle cover cup 120 and pushes the needle cover patient contact 181 against the body. This push force is designed to be well above the sensing threshold of the skin and is sensed by the patient. Therefore, patients also receive a haptic signal at the completion of injection. Additionally, the push by the needle cover patient contact 181 to the patient skin at the completion of injection, assists the removal of the device and its needle from the body.

Needle Cover Lock:

After release of the needle cover cup 120 and after the device is removed from the body, the needle cover cup 120 can eject completely. The ejection of the needle cover cup 120 is stopped when the needle cover guide 147 reaches and is stopped by the needle cover forward stops 137 in the bottom housing 108. At some point prior to this, the tip of the needle cover backstops 180 enters the needle cover backstop grooves 185, and the needle cover backstop cantilever 146 unbends for that. Beyond this point the ejected needle cover cup 120 is constrained from being inserted back into the device (e.g., via a backward or proximal motion), because the needle cover backstops 180 are engaged with the needle cover backstop supports 139, and the reaction normal force at their contact cancels the push force on the needle cover cup 120 in the backward or proximal direction.

The drug delivery device may include one or more of the following features:

A force transmitter piece that has two cylindrical gaps: an outer gap and an inner gap. The outer gap is located between the outer and inner cylindrical shells. The outer gap is closed at the distal end and is open at the proximal end. The inner gap is located between the drive rod and the inner cylindrical shell. The inner gap is open at the distal end and is closed at the proximal end.

An autoinjector device that its drive spring resides partially or fully inside the outer cylindrical gap of the force transmitter piece.

An autoinjector device that its syringe subassembly resides partially of fully inside the inner gap of the force transmitter piece.

An autoinjector device that has axial ribs on the outer surface of the force transmitter piece and axial conjugate axial slots on the inner surface of the housing, to be coupled with axial ribs.

An autoinjector device that coupling of the axial slots and axial ribs constraints the movement of the force transmitter piece to axial direction.

An autoinjector device in which there is a clearance between the outer surface of the axial ribs and inner surface of the axial slots, which is filled with a viscous material to form a damping mechanism.

An autoinjector device that has a flexible disk to provide a flexible support for the needle in axial direction.

An autoinjector device that uses a flexible support to increase the impact duration between the syringe and device and consequently to reduce the peak impact force.

An autoinjector device that uses a flexible support along with the damping mechanism to partially retract the needle after insertion.

An autoinjector device that uses a cylindrical release core to hold and then release the force transmitter.

An autoinjector with a release core that transforms the linear downward motion of the activation button to rotational motion of the release core.

An autoinjector device with a release core with 3 or more release hooks at its lower end.

An autoinjector device with a force transmitter that has 3 or more hold hooks and release hooks stops at its upper end.

An autoinjector device that the release hooks are engaged with hold hooks and release hook stops to hold the force transmitter against a compressed drive spring force.

An autoinjector device that some rotation of the release core disengages the release hooks and hold hooks and releases the force transmitter An autoinjector device that in at successful completion of injection, the plunger stopper is reached and stopped by the end of the barrel.

An autoinjector device that the length and diameter of the plunger rod and the dimensions of the inner shell of the force transmitter can be adjusted to make the device compatible to different barrels, different plunger stoppers and different fill volumes.

An autoinjector device with a needle cover mechanism that is activated at the end of injection and ejects a needle cover cup to cover the extended needle.

An autoinjector device with a needle cover cup that is secured to the device housing by two or more needle cover release hooks and cantilevers against the force of a compressed spring.

An autoinjector device with a needle cover cup that includes a needle cover release hook on a cantilever, in contact with the device, where the contact surfaces of the device and release hook may be flat or inclined.

An autoinjector device with a needle cover cup that contains backstop hooks on a cantilever.

An auto injector device that both backstop cantilevers and release cantilevers bend at start of the ejection of the needle cover cup and straighten after that causing the backstops and release hooks to impact the inner surface of bottom housing to generate audible end of delivery signals.

An autoinjector device with a needle cover cup that contains backstop hooks, where the backstop hooks engage with the housing bottom at the completion of needle cover ejection to prevent backward (e.g., returning) motion of the needle cover cup.

An autoinjector device with a needle cover cup that is released at the completion of injection and pushes the patient body to create a haptic end of delivery signal.

An autoinjector device with a needle cover cup that is released at the completion of injection and pushes the patient body to assist removal of the device and its needle from the patient body.

Figure 6A:
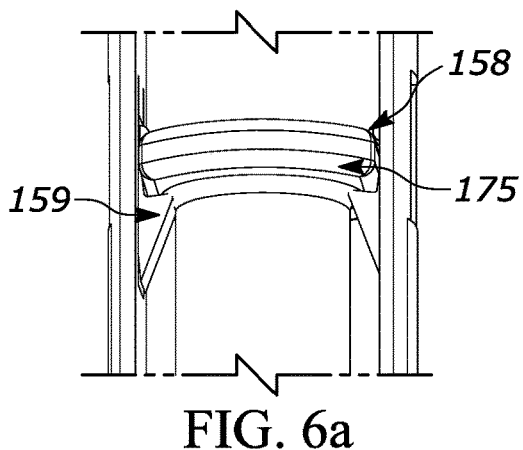
FIGS. 6a-6d show various views of different aspects of the syringe subassembly for a drug delivery device according to an embodiment of the present disclosure.
Figure 6B:
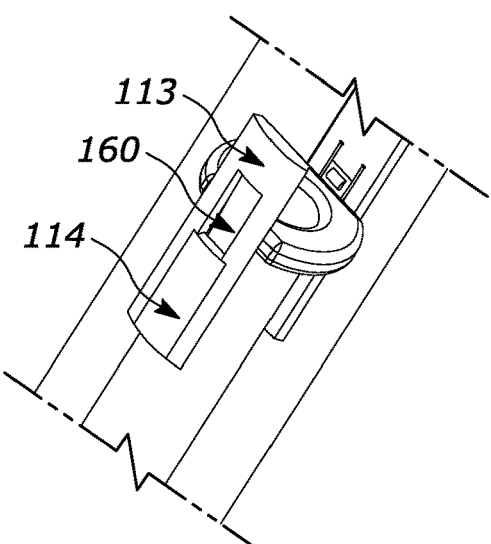
Figure 6C:
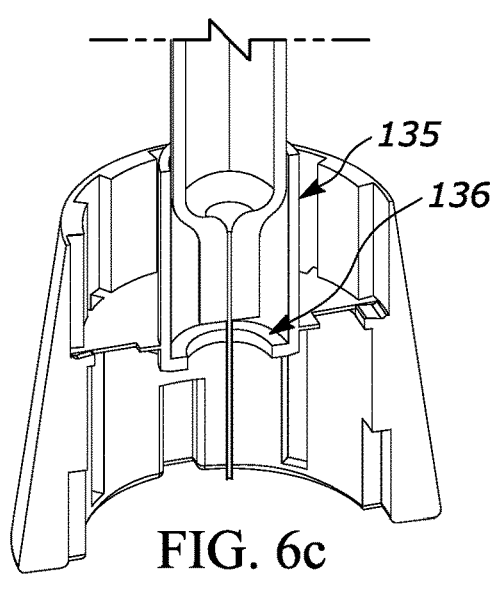
Figure 6D:
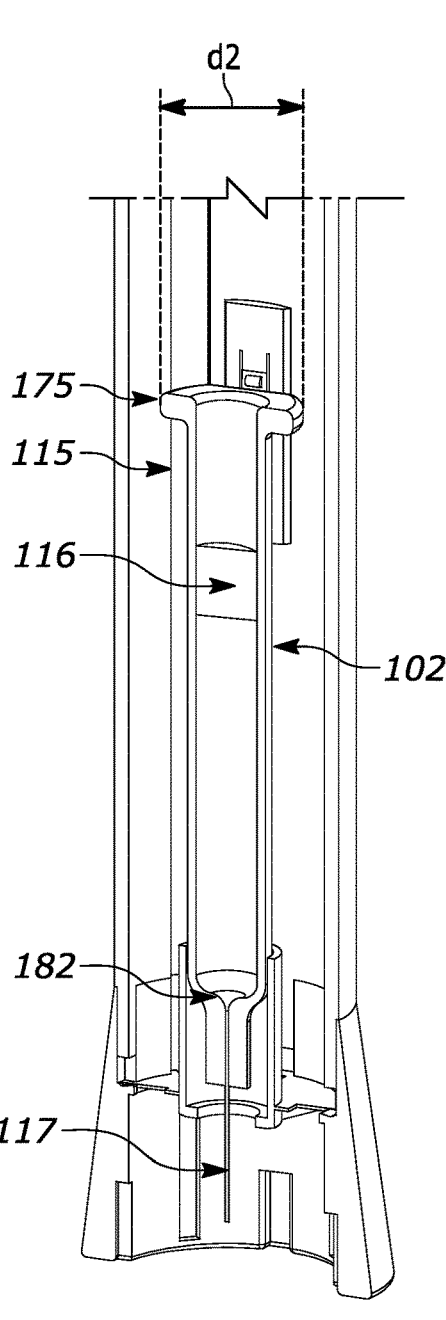
Figure 7A:
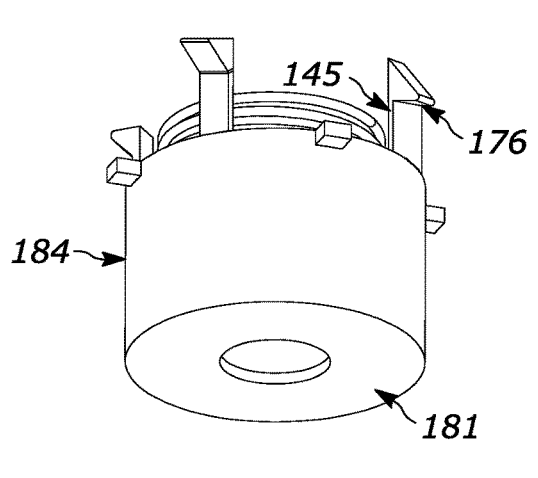
FIGS. 7a-7e show various views of different aspects of the needle cover subassembly for a drug delivery device according to an embodiment of the present disclosure.
Figure 7D:
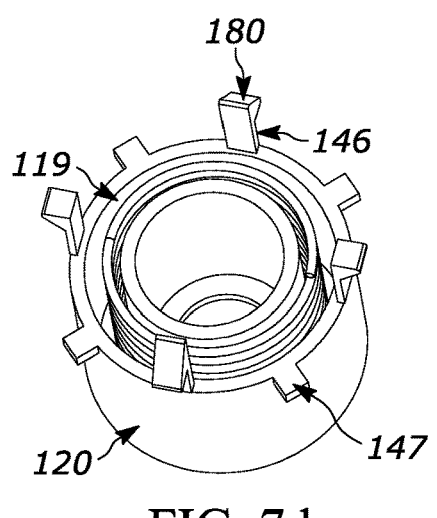
Figure 7B:
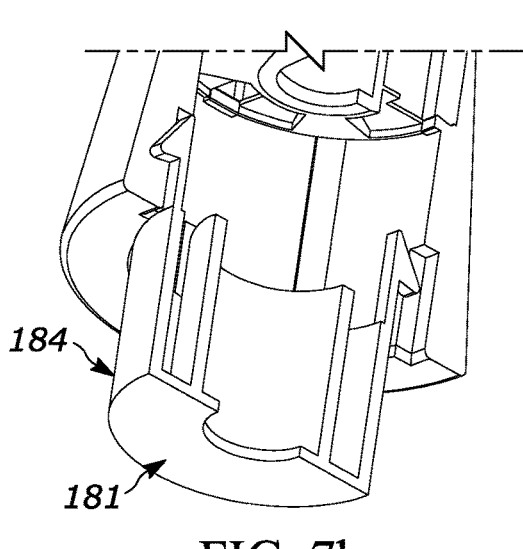
Figure 7E:
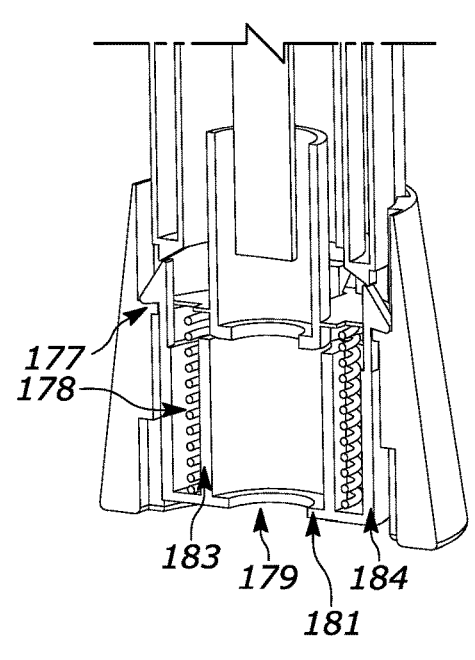
Figure 7C:
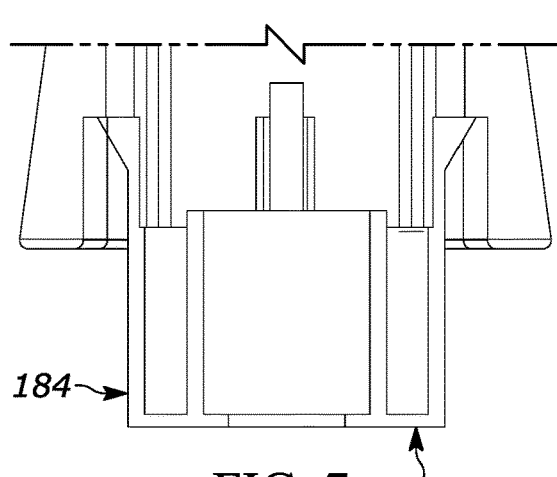
Figures 8, 9:
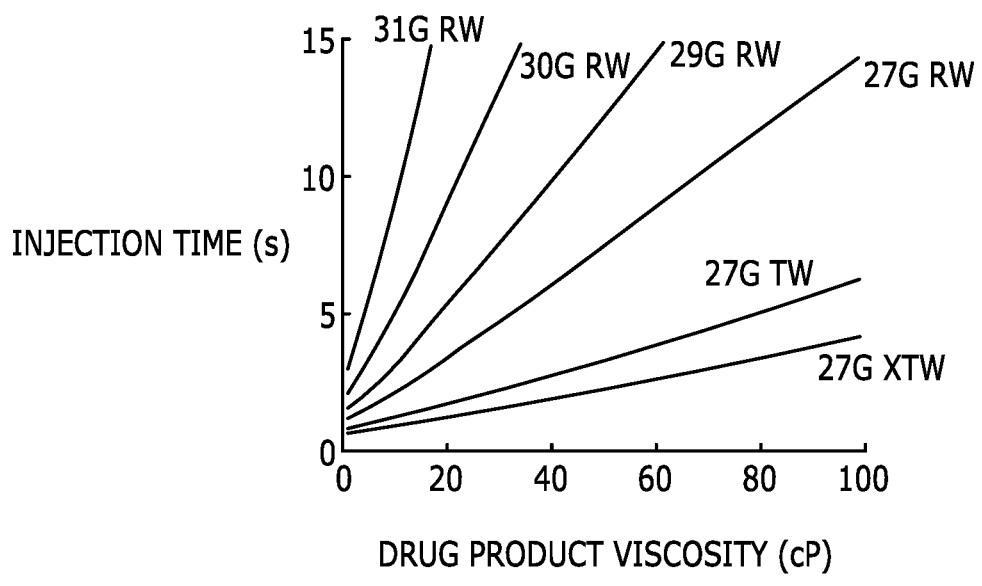
FIG. 8 is a graph plotting injection time vs. drug product viscosity for a drug delivery device according to an embodiment of the present disclosure. Each plotted line in FIG. 8 corresponds to the drug delivery device outfitted with a needle having a gauge identified adjacent to the plotted line.
FIG. 9 is a table of injection times (IT) measured in seconds (s) for various needle gauges and drug product viscosities for a drug delivery device according to an embodiment of the present disclosure.

The drug storage container is configured to contain a drug. The drug storage container may be pre-filled and shipped, e.g., by a manufacturer, to a location where the drug storage container is combined with a remainder of the drug delivery device. The housing may be pre-loaded with the drug storage container, e.g., by a manufacturer, or alternatively, loaded with the drug storage container by a user prior to use of the drug delivery device. The drug storage container may include a barrel 15 with rigid wall defining an internal bore or reservoir. The wall may be made of glass or plastic. Referring to FIG. 6*d*, the plunger stopper 116 may be moveably disposed in the barrel 15 such that it can move in a distal direction along the longitudinal axis between proximal end and a distal end of the barrel 115. The plunger stopper 116 may be constructed of rubber or any other suitable material. The plunger stopper 116 may slidably and sealingly contact an interior surface of the barrel wall such that the drug is prevented or inhibited from leaking past the plunger stopper 116 when the plunger stopper is in motion.

Distal movement of the plunger stopper 116 expels the drug from the barrel 115 into the delivery member. The proximal end of the barrel may be open to allow a plunger rod 156 to extend into the barrel 15 and push the plunger stopper 16 in the distal direction. In the present embodiment, the plunger rod 156 and the plunger stopper 116 are initially spaced from each other by a gap.

In the present embodiment, the drug storage container is a pre-filled syringe and has a staked, hollow metal needle 117 for the delivery member. Here, the needle 117 is fixed relative to the wall of the barrel 115 and is in permanent fluid communication with it. In other embodiments, the drug storage container may be a needle-less cartridge, and, as such, initially may not be in fluid communication with the delivery member. In such embodiments, the drug storage container may move toward a proximal end of the delivery member, or vice versa, during operation of the drug delivery device such that the proximal end of the delivery member penetrates through a septum covering an opening in the drug storage container thereby establishing fluid communication with the reservoir of the drug storage container.

The plunger may be constructed in multiple, interconnected pieces, or alternatively, have a one-piece construction. In the present embodiment, the plunger includes a rod having a threaded outer surface and washer or disk rigidly attached to a distal end of the rod. The disk may impact and push the stopper when the drive mechanism is activated. Accordingly, in some embodiments, the disk may have shock-absorbing properties to attenuate any shock or vibrations associated with the impact event.

From the foregoing, it can be seen that the present disclosure advantageously provides an improved drug delivery device that facilitates safe handling of the device in the post-delivery state and reduces the chances of incomplete dosing, as well as providing other benefits and advantages.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated fil-gastrim, pegylated G-CSF, pegylated hu-Met-G-CSF) and Neupogen® (filgrastim, G-CSF, hu-MetG-CSF), UDE-NYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating pro-tein. As used herein, "erythropoiesis stimulating protein" means any protein that directly or indirectly causes activa-tion of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoi-etin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epo-etin delta), Mircera® (methyoxy polyethylene glycol-epo-etin beta), Hematide®, MRK-2578, INS-22, Retacrit® (epo-etin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Epo-ratio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, ana-logs, variants or derivatives thereof: OPGL specific antibod-ies, peptibodies, related proteins, and the like (also referred to as RAN KL specific antibodies, peptibodies and the like), including fully humanized and human OPGL specific anti-bodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities medi-ated by binding of IL-4 and/or IL-13 to the receptor; Interleukin 1-receptor 1 ("IL1-R1") specific antibodies, pep-tibodies, related proteins, and the like; Ang2 specific anti-bodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully human-ized antibody in Epratuzumab, CAS registry number 501423-23-0; IGF-1 receptor specific antibodies, peptibod-ies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not lim-ited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related pro-teins, and the like, such as, in particular, humanized mono-clonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific anti-bodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepa-tocyte growth factor ("HGF") specific antibodies, peptibod-ies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific anti-bodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibod-ies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-va-line, 88-asparagine, 90-threonine], Darbepoetin alfa, novel erythropoiesis stimulating protein (NESP); Epogen® (epo-etin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion pro-tein, TNF blocker); Eprex® (epoetin alfa); Erbitux® (cetux-imab, anti-EGFR/HER1/c-ErbB-1); Genotropin® (somatro-pin, Human Growth Hormone); Herceptin® (trastuzumab, anti-HER2/neu (erbB2) receptor mAb); Kanjinti™ (trastuzumab-anns) anti-HER2 monoclonal antibody, bio-similar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immuno-globulin G2 Human Monoclonal Antibody to RANK Ligand, Enbrel® (etanercept, TNF-receptor/Fc fusion pro-tein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Ben-lysta™ (lymphostat B, belimumab, anti-BlyS mAb); Metal-yse® (tenecteplase, t-PA analog); Mircera® (methoxy polyethylene glycol-epoetin beta); Mylotarg® (gemtuzumab ozogamicin); Raptiva® (efalizumab); Cimzia® (certoli-zumab pegol, CDP 870); Soliris™ (eculizumab); pexeli-zumab (anti-C5 complement); Numax® (MEDI-524); Lucentis® (ranibizumab); Panorex® (17-1A, edrecolomab);

Trabio® (lerdelimumab); TheraCim hR3 (nimotuzumab); Omnitarg (pertuzumab, 2C4); Osidem® (IDM-1); Ova-Rex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Rα mAb (Hu-Max-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TI MP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-yl-carbamoyl)-2-phenylethyl)-2-((S)-2-(2-morpholinoacet-amido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acet-amide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRASG12C small molecule inhibitor, or another product containing a KRASG12C small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)× anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BiTE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3

BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
a housing having an opening;

a drug storage container having an inner surface at least partially defining a drug storage chamber, an outer surface defining an outer diameter, a plunger stopper, and a delivery member having an insertion end configured to extend at least partially through the opening during a delivery state;

a plunger rod;

a drive mechanism configured to generate a force for driving the plunger stopper in a distal direction to expel a drug from the drug storage container through the delivery member, the drive mechanism having an inner surface with an inner diameter greater than the outer diameter of the outer surface of the drug storage container; and a force transmitter functionally coupled with the drive mechanism and the plunger stopper to transfer the force of the drive mechanism to the plunger stopper, wherein the force transmitter includes an inner cylindrical shell and an outer cylindrical shell, wherein at least the outer cylindrical shell is configured to move with respect to the housing.

2. The drug delivery device of claim 1, wherein the drive mechanism is initially compressed, and following device activation, decompresses over at least a portion of the drug storage container.

3. The drug delivery device of claim 1, wherein the force transmitter includes a drive rod, wherein each of the inner cylindrical shell and the outer cylindrical shell is coaxial with the drive rod.

4. The drug delivery device of claim 3, wherein the drive rod is at least partially disposed within the inner cylindrical shell.

5. The drug delivery device of claim 1, comprising a gap radially between the inner cylindrical shell and the outer cylindrical shell, wherein the drive mechanism is at least partially disposed in the gap.

6. The drug delivery device of claim 1, wherein a distal end of the drive mechanism is configured to bear upon an inner surface of the force transmitter.

7. The drug delivery device of claim 6, wherein the inner surface is disposed radially between the inner cylindrical shell and the outer cylindrical shell.

8. The drug delivery device of claim 1, wherein an inner diameter of the inner cylindrical shell is greater than the outer diameter of the outer surface of the drug storage container.

9. The drug delivery device of claim 8, wherein the inner diameter of the inner cylindrical shell is less than the inner diameter of the inner surface of the drive mechanism.

10. The drug delivery device of claim 1, wherein, upon activation, the drive mechanism moves the force transmitter in the distal direction.

11. The drug delivery device of claim 1, wherein the drive rod of the force transmitter comprises the plunger rod such that the drive rod of the force transmitter and the plunger rod define a single, one-piece component.

12. The drug delivery device of claim 1, wherein the drug storage container is moveable relative to the housing and has an initial position wherein the insertion end of the delivery member is disposed within the housing and a second position wherein the insertion end of the delivery member extends at least partially through the opening in the housing.

13. The drug delivery device of claim 12, wherein, upon activation, the drive mechanism moves the drug storage container from the initial position to the second position.

14. The drug delivery device of claim 1, wherein the drive mechanism comprises a spring.

15. The drug delivery device of claim 14, wherein the spring is a compression spring.

\* \* \* \* \*